United States Patent [19]
Seebach et al.

[11] Patent Number: 5,386,035
[45] Date of Patent: Jan. 31, 1995

[54] METHOD OF PRODUCING OPTICALLY ACTIVE 1,3-IMIDAZOLIDINE-4-ONES

[75] Inventors: Dieter Seebach, Zürich, Switzerland; Karlheinz Drauz, Freigericht, Germany; Matthias Kottenhahn, Hanau, Germany; Hermann Lotter, Hainburg, Germany; Michael Schwarm, Alzenau, Germany

[73] Assignee: Degussa Aktiengesellschaft, Germany

[21] Appl. No.: 974,422

[22] Filed: Nov. 12, 1992

[30] Foreign Application Priority Data

Nov. 12, 1991 [DE] Germany .............................. 4137186
Nov. 15, 1991 [DE] Germany .............................. 4137663

[51] Int. Cl.6 .................. C07D 233/38; C07D 233/32; C07D 233/30; C07K 5/00
[52] U.S. Cl. ............................... 548/316.4; 548/324.1; 548/322.5
[58] Field of Search ................ 548/316.4, 322.5, 324.1

[56] References Cited

U.S. PATENT DOCUMENTS

| | | | |
|---|---|---|---|
| 4,280,008 | 7/1981 | Schoellkopf et al. | 548/316.4 |
| 5,210,210 | 5/1993 | Davies | 548/316.4 X |

FOREIGN PATENT DOCUMENTS

| | | | |
|---|---|---|---|
| 0137351 | 9/1984 | European Pat. Off. | 548/316.4 |
| 0237630 | 11/1986 | European Pat. Off. | 548/316.4 |
| 3604591 | 8/1987 | Germany | 548/316.4 |

OTHER PUBLICATIONS

Naef et al, Helv. Chim Acta, vol. 68, pp. 135 to 143 (1985).
Angewandt Chemie, Bd. 98, Nr. 4, 1986, Weinheim pp. 363-364 Fitzi et al I.
Tetrahedron Bd. 44, Nr. 17, 1988, Great Britain pp. 5277-5292 Fitzi et al II "Resolution and use in alpha-amino acid synthesis of imidazolidinone glycine derivatives".
Liebigs Annalen Der Chemie 1989, Weinheim pp. 1215-1232; Dieter Seebach et al. III "Synthesis of Non-proteinogenic (R)-or (S)-Amino acids Analogues of Phenylalanine, ...".
Enantiomers, Racemates, and Resolutions by Jean Jacques and Andre Collet publication pp. 309-312 (1981).
Article entitled "Diastereoselective Cyclization of a Glycil-alanine Azomethine to an Imidazolidinone: Determination of the Product Configuration by X-Ray Analysis" 1989 by Martin Egli, Robin Polt and Dieter Seebach pp. 4 and 5.

*Primary Examiner*—Floyd D. Higel
*Attorney, Agent, or Firm*—Cushman, Darby & Cushman

[57] ABSTRACT

2.2. 1,3-imidazolidine-4-ones having the General Formula:

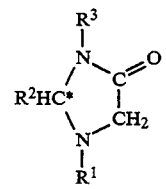

are obtained in a pure form especially by means of precipitation, in which production an optically active acid can be used at 0.5–0.8 eq. for the separation of racemates. The non-desired enantiomer can be racemized in an inert solvent and the cyclization to imidazolidinone can take place by means of the optically active acid, whereupon the separation of racemates takes place directly thereafter. 1,3-imidazolidine-4-ones are valuable educts for the preparation of branched or unbranched, proteinogenic or non-proteinogenic α-amino acids by means of diastereoselective alkylation and subsequent ring splitting.

11 Claims, No Drawings

METHOD OF PRODUCING OPTICALLY ACTIVE 1,3-IMIDAZOLIDINE-4-ONES

The invention relates to a method of producing enantiomerically pure 1,3-imidazolidine-4-ones which have the general formula:

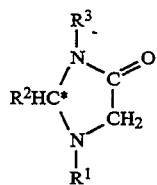

I in which * is a center of asymmetry to which the enantiomeric purity refers, $R^1$ is H or a group which can split off in the acidic, e.g. Boc⁻, Z⁻ or Bz⁻, $R^2$ is a sterically hindering group which contains at least 3 carbon atoms, e.g. iso-propyl- or tert-butyl-, and $R^3$ is an organic group which contains 1–10 carbon atoms, preferably 1–4 carbon atoms, e.g. methyl-, ethyl-, propyl-, benzyl-, and also amino acid groups. The method includes racemic resolution of a racemic 1,3-imidazolidine-4-one with the general formula

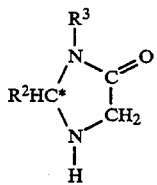

II in which $R^2$ and $R^3$ have the meaning already indicated and optional subsequent substitution of the hydrogen on the nitrogen of the enantiomer obtained, for the introduction of a group which can split off under acidic conditions. $R^1$ and $R^3$ can be substituted with aliphatic and/or aromatic groups, depending on of the method and $R^B$ essentially has the function of acylation protection. The invention also comprises the use of the products produced by this method.

Such methods are known from German Patents DE 33 34 855 and DE 36 04 591 A1 as well as from D. Seebach et al., Helv. Chim. Acta 68, pp. 135, 949 (1985), D. Seebach et al., Angew. Chem. 98, p. 363 (1986) and D. Seebach et al. Tetrahedron 44, p. 5277 (1988).

The 1,3-imidazolidine-4-ones constitute an interesting group of compounds which are valuable educts for the preparation of branched or unbranched proteinogenic or non-proteinogenic amino acids by means of single or twice-repeated diastereoselective alkylation and subsequent ring splitting. These amino acids can be incorporated into peptides or used in amino acid mixtures such as infusion solutions. Since these compounds or preparations find use as pharmaceutical products, it is desirable to be able to prepare 1,3-imidazolidine-4-ones as economically as possible, and especially in as high a purity as possible.

Known methods have a problem in this respect, because a considerable number of individual steps is necessary in which oily intermediate products occur rather than crystal-line ones. For this reason, these methods are either not suitable or suitable only to a limited extent for the preparation of 1,3-imidazolidine-4-ones on a rather large scale.

The object of the present invention is to provide a method with which products, which are enantiomerically pure and as free from impurities as possible, can be obtained in as economical a manner as possible. A further object is to minimize expensive method steps such as e.g. extractions and solvents whose use may be undesirable, such as e.g. di- or trichloromethane. Depending on the cost of the starting materials, an optimization as regards the necessary method steps, the yield and/or the purity of the 1,3-imidazolidine-4-ones obtained in this manner should be possible. In addition, the enantiomerically pure 1,3-imidazolidine-4-ones obtained in this manner should be able to be used for the production of enantiomerically pure amino acids.

These and other objects are achieved by a method of producing enantiomerically pure 1,3-imidazolidine-4-ones with the general formula:

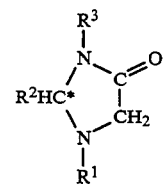

I in which * is a center of asymmetry to which the enantiomeric purity refers, $R^1$ is H or a group which can split off in the acidic, $R^2$ is a sterically hindering group which contains at least 3 carbon atoms and $R^3$ is an organic group which contains 1–10 carbon atoms by means of the racemic resolution of a racemic 1,3-imidazolidine-4-one with the general formula

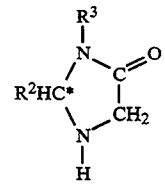

II in which $R^2$ and $R^3$ have the meaning already indicated and optional subsequent substitution of the hydrogen on the nitrogen of the enantiomer obtained for the introduction of the group which can split off under acidic conditions. In accordance with the method of the invention, the 1,3-imidazolidine-4-one of General Formula II is treated as a salt with a solvent and a base in which the 1,3-imidazolidine-4-one of general formula II is soluble causing a salt to precipitate from a cation of the base and an anion of the salt of the 1,3-imidazolidine-4-one. The precipitated salt is separated and the dissolved 1,3-imidazolidine-4-one is supplied to a separation of racemates.

As compared to the previously known methods, the novel method permit a simpler, more economical, more rapid and less waste-producing production of compounds of General Formula I which can be used for the enantioselective synthesis of amino acids. On the other hand, the novel methods can stop at an intermediate stage for the production of educts known from the cited literature.

Basically, one can start for the educts of the methods of the invention with an alkyl ester of the amino acid glycine, preferably the methylester, in the form of its hydrochloride, which is reacted in a lower alcohol with a lower monoalkylamine in a known manner to the corresponding glycine alkylamide hydrochloride III.

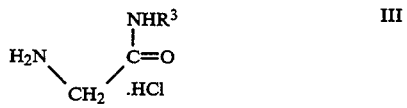

The latter is condensed in a known manner with an aldehyde in the presence of an amine base such as e.g. triethylamine by means of boiling with a suitable solvent, e.g. methyl-t-butylether or a chlorinated or non-chlorinated hydrocarbon, on a water separator to the Schiff's base IV, during which the $R^2$ group, which is preferably tert-butyl-or iso-propyl-, is introduced via the aldehyde

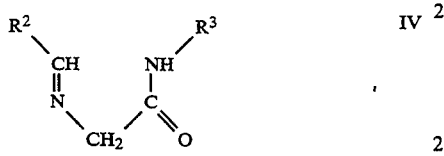

The amine hydrochloride arising is filtered and the filtrate containing the Schiff's base cyclized in a suitable solvent such as an ether, a chlorinated or non-chlorinated hydrocarbon or an alcohol, preferably methanol, ethanol or isopropanol with a suitable, usually strong acid, preferably anhydrous HCl gas. It is advantageous if the formed salt of the racemic 1,3-imidazolidine-4-one is precipitated at this stage by cooling off and it is then separated by filtration, for which the type and the amount of the solvent are to be adjusted in a suitable manner. Here and in the following discussion, the term "salt of 1,3-imidazolidine-4-one" denotes an addition compound with an acid such as e.g. HCl or mandelic acid. The compound of General Formula II can be obtained in high yields and especially in very great purity by means of this crystallization. It was found, in this connection, that this is a condition for the success of the subsequent resolution of racemates. Moreover, the compound of General Formula II can be stored for a rather long time as salt without decomposition, in contrast to the free base. Compared to the previous methods (DE 36 04 591 A1 and "Tetrahedron"), a finely crystalline intermediate product is isolated which influences the quality and in some instances also the yield of the desired product in a decidedly advantageous manner.

The racemic 1,3-imidazolidine-4-one II can subsequently be liberated from its salt, in a known and simple manner, by means of reaction with a base. In the past, instead of this, if such a salt was obtained as an intermediate, it was combined with an aqueous base and the free base was extracted with methylene chloride. This solvent had to be removed again by distillation and replaced by acetone for the subsequent resolution of racemates.

According to the invention the extraction step can be eliminated by suspending the salt preferably in acetone and combining it with a stoichiometric amount of an anhydrous base, e.g. an amine base, preferably triethylamine or with a concentrated aqueous solution of a base such as sodium- or potassium hydroxide or the salt of an organic acid such as sodium mandelate. The free 1,3-imidazolidine-4-one is soluble in the system produced, whereas the salt precipitates almost quantitatively from the cation of the base and from the anion of the salt of II and can be separated by filtration. The water still present in the acetone from the use of the aqueous solution of the base does not interfere with the subsequent resolution of racemates.

The resolution of racemates can be carried out in a known manner by means of the addition of an optically active acid (DE 36 04 591 A1) such as e.g. mandelic acid. According to the invention, it was found that it is sufficient if the optically active acid is used in this connection in only 0.5–0.8 equivalents relative to the racemic 1,3-imidazolidine-4-one of General Formula II, whereas one equivalent or more was used previously.

In this manner up to 50% and more of the cost for this expensive chiral auxiliary compound can be saved. During the cooling off of the solution one of the diastereomeric salts then crystallizes out of the cation of the compound of General Formula I and the anion of the chiral acid and can be separated by filtration. The optical purity is in general so high that a recrystallization can be eliminated.

The salt can now be suspended in a solvent in accordance with the invention in a manner analogous to the procedure already described above in which solvent the free, optically active 1,3-imidazolidine-4-one of general formula I (R1=H) is soluble. A salt precipitates from the cation of an added base such as e.g. sodium hydroxide solution or potassium hydroxide solution or an amine base such as triethylamine and from the anion of the optically active acid. Acetone is again particularly suitable here. After the reaction is over, this salt is separated by filtration and the dissolved 1,3-imidazolidine-4-one of formula I (R1=H) can be reacted with an acylating agent such as an acid chloride V, an acid anhydride VI, a carbonic ester chloride VII or a pyrocarbonic diester VIII in order to introduce in a basically known manner the group which can be split off under aid conditions. $R^1$ signifies a group capable of being split off under acidic conditions and specified in the case of the particular reagent, e.g. Boc-, Z- or Bz-, and $R^4$ a branched or unbranched, substituted or unsubstituted alkyl group (e.g. t-butyl) or aryl group (e.g. phenyl or benzyl).

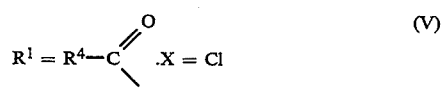

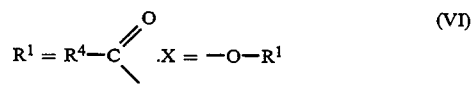

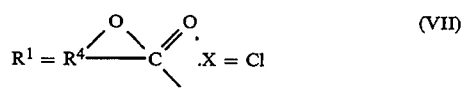

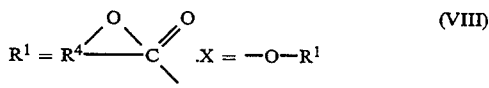

The water remaining in acetone when sodium hydroxide is used to liberate the 1,3-imidazolidine-4-one surprisingly does not interfere with the acylation of I with V, VI, VII or VIII. The special advantage of this non-extractive method resides in the fact that it is not necessary to use a chlorinated hydrocarbon such as chloroform or methylene chloride, which is otherwise almost unavoidable, for the extraction of the free, enantiomerically pure 1,3-imidazolidine-4-one I, which is unsubstituted on the N-1, from aqueous solution. This is an important advantage for both for reasons of environmental protection, expense and health, particularly in large-scale industrial methods and which considerably reduces the engineering costs.

A further advantage of this method is the fact that the salt from the cation of the added base and from the anion of the chiral acid can be recovered by filtration and directly reused in the form of a concentrated aqueous solution for further resolutions of racemates. Therefore, special operations of workup or purification for recovery of the valuable, optically active acid from this reaction step are unnecessary.

After the substitution has been carried out, according to the invention the reaction product is taken up in a solvent which is not readily miscible with water and from which the reaction product can be crystallized. Hydrocarbons such as e.g. n-hexane or cyclohexane but also petroleum ethers with various boiling ranges are especially suitable here. The solution of the product is then washed with water. This separates, for the most part, the products produced during the acylation such as HCl $R_4COOH$ or $R_4OH$, which otherwise disturb the subsequent crystallization of the product and can thus reduce the yield.

Alternatively or in addition to the latter step, a part of the solvent can be distilled off, in which instance the distillation is preferably carried out after the previously mentioned step. During this procedure, the above-named by-products of the acylation are separated even further, that is, practically completely.

In this method, the imidazolidinone of formula II can be combined advantageously, after the resolution of racemates in an aqueous system, with an organic solvent which is miscible with water (e.g. acetone). The group which can be split off under acidic conditions is subsequently introduced in this system, the organic solvent is separated off and the product is taken up with the solvent which is not freely miscible with water.

For workup, the enantiomerically pure 1,3-imidazolidine-4-one substituted on the N-1 and having the General Formula I is crystallized by cooling and is separated by filtration. This method generates a finely crystalline, very clean product in one step and in high yield which generally does not require further recrystallization. In contrast, according to the previously known methods, an oil was obtained at first which had to be brought to crystallization, which is very expensive, especially on an industrial scale.

An especially advantageous variant of the invention is the substitution (the introduction of the group $R_1$, splittable under acidic conditions, with $R_1 = H$) after the resolution of racemates in an aqueous-organic 2-phase system. After the substitution, the imidazolidinone of General Formula I is in the organic phase and can be separated from the aqueous phase. The aqueous phase contains, among other things, the (R)-mandelic acid (to the extent it was used) in the form of a salt which can be isolated (and recycled) e.g. by means of acidification. In contrast to the previous methods, in which the substitution required expensive purification and drying steps, a crystallizable product is obtained with distinctly less expense. An especially favorable feature of this variant is the fact that, given a suitable selection of the organic phase, the product can be crystallized directly from this phase (optionally after evaporation of the phase to low volume). Moreover, this variant can be carried out advantageously with an organic phase which has a lesser or equal solubility for the imidazolidinone of General Formula II than water. This makes it possible to avoid halogenated solvents.

The mother liquor remaining from the resolution of racemates of the racemic 1,3-imidazolidine-4-one II contains the second enantiomer in enriched form, which, if desired, can be isolated according to known methods in pure form (DE 36 04 591 A1). However, there is frequently a need for only one enantiomer, so that it is economically as well as ecologically advantageous to be able to racemize the enantiomer which is not desired, in order to better utilize this expensively synthesized intermediate product, i.e., utilize more than a maximum of 50% of it.

For the racemization, the free 1,3-imidazolidine-4-one isolated according to an extractive or non-extractive method from the mother liquor of the resolution of racemates, or as salt, is taken up according to the invention in an inert, preferably high-boiling solvent, e.g. a polyether. It is then racemized by heating, during which the temperature and the time of this reaction are adjusted in accordance with the stability and the speed of racemization of the 1,3-imidazolidine-4-one in the solvent used. In general, the required temperature is between 50° C. and 5K below the decomposition point of the enantiomer used. After cooling, this solution is added drop-by-drop into the solution of an anhydrous acid in a lower alcohol, e.g. HCl gas in methanol. The salt of the racemic 1,3-imidazolidine-4-one of General Formula II can then be crystallized and isolated in high yield by filtration.

It is also possible, as an alternative, to first produce a salt of the 1,3-imidazolidine-4-one, in which an enantiomer is enriched, and then to dissolve or suspend it in an inert, preferably high-boiling solvent such as e.g. a polyether, and finally to racemize it by heating. The temperature and time of the reaction are adjusted according to the stability and the racemization speed of the salt in the solvent used. In general, the temperatures are, as in the preceding method, between 50° C. and 5 K below the decomposition point of the enantiomer or of its salt in the solvent. After cooling, the salt of the racemic 1,3-imidazolidine-4-one of General Formula II is filtered off and, if necessary, purified by means of recrystallization. These methods have the advantage over the previously described racemization by means of heating the free base (D. Seebach, Angeu Chem. 102, 1363 (1990)) because they take place substantially without decomposition, supply good yields as a result and in particular can also be carried out smoothly on an industrial scale. It is particularly surprising that the salt of the 1,3-imidazolidine-4-one can be racemized while suspended in a solvent, since the salt as such (without solvent) is not capable of racemization.

The previously described method variants can be combined with each other to a large extent, as explained, and each is suitable either alone or in any desired combination for replacing the corresponding method steps like those which were previously conventional, which gives rise to the advantages of the invention.

If very clean chemicals and exactly controlled reaction conditions are used, it was surprisingly noticed that the method can be simplified even further by carrying out the cyclization of the Schiff's base IV to the racemic 1,3-imidazolidine-4-one II and the resolution of racemates in one step using the same optically active acid. For this, the Schiff's base is produced as described above, taken up in a suitable solvent, especially in a lower alcohol, and added drop-by-drop to the solution of the optically active acid in preferably the same solvent. After the end of the reaction, the solvent is distilled off and replaced by one in which the differences in solubility between the diastereomeric salts to be separated are as great as possible (e.g. acetone). In principle, the process can also be carried out in one solvent; however, yield losses usually result in the first or second step. The desired salt then crystallizes out in the required purity during cooling, usually without a further recrystallization being necessary. The yield in this one-stage method is comparable to the multi-stage process described above; however, the circuitous path via the salt of 1,3-imidazolidine-4-one and the necessary liberation of the base associated therewith is eliminated. Again, the method steps described above can be combined with this "rapid method".

The methods described above offer on the whole a considerably simplified and industrially practical route to enantiomerically pure 1,3-imidazolidine-4-ones of the General Formula I while requiring less time and expensive starting materials than in the past and drastically reducing the unavoidable amount of by-products. In particular, the use of halogenated hydrocarbons can be partially or completely eliminated, depending on the combination of the individual variants. The methods steps of the invention make it economical to carry out the known method for producing the compound of General Formula I on an industrial scale.

The imidazolidinones obtained are useful for the production of enantiomerically pure, branched or unbranched, proteinogenic or non-proteinogenic α-amino acids as well as peptides or amino acid mixtures containing these amino acids. For this purpose, the imidazolidinones obtained are advantageously alkylated diastereoselectively in a known manner. The corresponding α-amino acid can then be obtained from the alkylated product in a known manner by means of ring splitting, which acid can then be reacted further—e.g. inserted into a peptide—or used in some other manner—e.g. in an amino-acid mixture. (W. Muller, D.A. Lowe, H. Neijt, S. Urwyler, P. L. Herrling, D. Blaser, D. Seebach, Helv. Chim. Acta 1992, 75, pp. 855; D. Seebach, E. Dziadulewicz, L. Behrendt, S. Cantoreggi, R. Fitzi, Liebigs Ann. Chem. 1989, p. 1215; R. Fitzi, D. Seebach, Tetrahedron 1988, 44, pp. 5277).

DETAILED DESCRIPTION OF PREFERRED EMBODIMENTS

The methods of the invention are described in more detail in the following examples:

EXAMPLE 1 (Starting Material)

Production of (R,S)-2-(t-butyl)-3-methyl-1,3-imidazolidine-4-one hydrochloride 125.6 g (1.0 mole) glycine methylester hydrochloride were charged into a solution of 77.5 g (2.5 moles) monomethylamine in 618 ml methanol at room temperature and the resulting solution was agitated overnight at room temperature. Then a major part of the methanol was distilled off under a slight vacuum and, after the addition of 250 ml cyclohexane, the remaining methanol was separated azeotropically. The residue was combined with 300 ml methyl-t-butyl ether, 167 ml (1.5 moles) pivalaldehyde and 152 g (1.5 moles) triethylamine and heated 8.5 hours on a water separator under reflux, during which time 24.5 ml water were separated. Then, the ether was distilled off and the Schiff's base remaining as a residue was taken up in 100 ml ethanol.

Then, 332 g of a 13.2% solution of HCl (1.2 moles) in ethanol was added drop-by-drop to the solution while cooled with ice during 45 min. After 15 minutes, fine white crystals separated. In order to complete the precipitation, another 80 ml ethanol were distilled off at 175 mbars and 400 ml methyl-t-butyl ether added drop-by-drop. After 1.5 hours of agitation in an ice bath, the solid was suction filtered, washed with 150 ml methyl-t-butyl ether and dried in a vacuum drying oven at 35° C.

Yield: 123.0 g (63.8%) Melting point: 185.0°–186.5° C. $C_8H_{17}ClN_2O$ calc. C 49.86 H 8.89 N 14.58 Cl18.40 MG: 192.7 obs. C 49.80 H 9.11 N 14.21 Cl18.36 $^1H$-NMR (500 MHz, $d^6$-DMSO): 1.1 ppm (s, 9H, $C(CH_3)_3$), 2.9 (s, 3H, $NCH_3$), 3.8 (AB system, 2H $CH_2$), 4.7 (s, 1H NCHN), 10.4 ( br s, 2H $NH_2^+$)

EXAMPLE 2

Enantiomeric separation of (R, S) -2- (t-butyl) -3-methyl-1,3-imidazolidine-4-one after liberation with triethylamine 20.3 g (0.2 mole) triethylamine was added drop-by-drop under agitation to a suspension of 38.5 g (0.2 mole) (R,S)-2-(t-butyl)-3-methyl-1,3-imidazolidine-4-one hydrochloride in 200 ml acetone, at which time a slight warming was observed. After 1 hour agitation at room temperature, the precipitated triethylamine hydrochloride was removed by suction and washed with 50 ml acetone. 30.4 g (0.2 mole) (R)-mandelic acid were then firmly charged into the filtrate. The resulting clear, yellowish solution was then evaporated to low volume under a slight vacuum and 40° C. bath temperature to approximately 200 ml, cooled down to 0° C. and agitated 1.5 hours longer. The crystals of (R)-2-(t-butyl)-3-methyl-1,3-imidazolidine-4-one- (R)-mandel ate which precipitated after seeding were removed by suction, washed with 25 ml acetone and dried in a vacuum drying oven a t 50° C.

Yield: 15.3 g (49.7%) Optical purity (GC, TFA derivative, chirasil-val): 99.86% (R)-I ($R^1$=H) Analytical data: R. Fitzi, D. Seebach, Tetrahedron 44, pp. 5277–5292, 1988

EXAMPLE 3

Enantiomeric separation of (R,S)-2-(t-butyl)-3-methyl-1,3-imidazolidine-4-one after liberation with sodium hydroxide solution 10 g (0.125 mole) 50% sodium hydroxide solution were slowly added drop-by-drop to a suspension of 24.1 g (0.125 mole) (R,S)-2-(t-butyl)-3-methyl-1,3-imidazolidine-4-one hydrochloride in 185 ml acetone. After 20 minutes, 24.1 g of the hydrochloride and three batches of 10 g sodium hydroxide solution were added in succession so that a total of 96.4 g (0.5 mole) of hydrochloride and 40.0 g (0.5 mole) sodium hydroxide solution were used. The mixture was then agitated 90 minutes, NaCl filtered off and the batch heated to approximately 55° C. Then 76.0 g (0.5 mole) (R)-mandelic acid were added. The resulting clear yellow solution was then cooled overnight to 5° C., the colorless (R)-2-(t-butyl)-3-methyl-1,3-imidazolidine-a-one-(R)-mandel ate which crystallized out was filtered off, washed with a little cold acetone and dried in a vacuum drying oven at approximately 50° C.

Yield: 54.3 g (70.4%) Analytical data: See Example 2.

EXAMPLE 4

Enantiomeric separation of (R,S)-2-(t-butyl)-3-methyl-1,3-imidazolidine-4-one with 0.5 equivalents mandelic acid A solution of 1.56 g (0.010 mole) (R,S)-2-(t-butyl)-3-methyl-1,3-imidazolidine-4-one in 5 ml acetone was added to a solution of 0.76 g (0.005 mole) (R)-mandelic acid in 5 ml acetone, at which time a crystalline paste spontaneously formed. A clear yellow solution was obtained by heating to approximately 50° C. from which colorless, finely crystalline (R)-2-(t-butyl)-3-methyl-1,3-imidazolidine-4-one precipitated during slow cooling to 5° C., and it was filtered off, washed five times with 1 ml cold acetone per time and dried in a vacuum drying oven at approximately 50° C.

Yield: 0.99 g (84.2%) Optical purity (GC, TFA derivative, chirasil-val): 99.15% (R)-I (R$^1$=H)

EXAMPLE 5

Preparation of (S)-1-(t-butoxycarbonyl)-2-(t-butyl)-3-methyl-1,3-imidazolidine-4-one 80.0 g (1.0 mole) 50% sodium hydroxide solution were added drop-by-drop with agitation to a suspension of 308.3 g (1.0 mole) (R)-2-(t-butyl)-3-methyl-1,3-imidazolidine-4-one-(R)-mandelate in 1.2 liters of acetone. After 1 hour reaction time at room temperature, the insoluble sodium-(R)-mandelate was filtered off, washed with 150 ml acetone and dried in a vacuum drying oven at approximately 50° C.

Yield: 159.6 g (91.6%) [α]$^{20}_D$:−143.5°(c=2, 2N HCl)

The filtrate was combined, within 45 minutes, with ice cooling, with 229.0 g (1.05 moles) di-(t-butyl)pyrocarbonate ("Diboc"). After a brief period of agitation, the acetone was distilled off, the residue taken up in 300 ml n-hexane and washed with 150 ml water. Then, the hexane was distilled off, the residue taken up again in 500 ml n-hexane and cooled overnight to 5° C. The (S)-1-(t-butoxycarbonyl)-2-(t-butyl)-3-1,3-imidazolidine-4-one which crystallized out was filtered off, washed with 150 ml of cold n-hexane and dried in a vacuum drying oven at room temperature. Evaporation of the mother liquor to low bulk yielded a further charge of the same compound which was isolated as described.

Yield: 80.3 g+95.8 g=176.1 g (68.7%) [α]$^{20}_D$: 1st charge −14.95 2nd charge−14.70 Analytical data: R. Fitzi, D. Seebach, Tetrahedron 44, pp. 5277–5292, 1988.

EXAMPLE 6

Racemization of 2-(t-butyl)-3-methyl-1,3-imidazolidine-4-one

A solution of 50.0 g (0.26 mole) of optically active 2-(t-butyl)-3-methyl-1,3-imidazolidine-4-one hydrochloride ([α]$^{20}_D$: +28.1°) and 10.38 g (0.26 mole) sodium hydroxide in 125 ml water was extracted with 450 ml and again with 100 ml dichloromethane. The extraction agent was then distilled off, the residue taken up in 100 ml diethylene glycol dimethyl ether and agitated at 150°–155° C. bath temperature for 7 hours under an inert atmosphere.

The cooled solution was then added drop-by-drop with agitation into a solution of 11.0 g (0.30 mole) HCl in 128 ml methanol at which time a creamy white precipitate rapidly formed. After the mixture had cooled to 5° C., the precipitated 2-(t-butyl)-3-methyl-1,3-imidazolidine-4-one hydrochloride was filtered off, washed colorless with 300 ml methyl-t-butyl ether and dried in a vacuum drying oven at approximately 50° C.

Yield: 39.44 g (78.9%) [α]$^{20}_D$: 0 (c=2, MeOH) Analytical data: See Example 1.

It was possible to obtain further product by adding 500 ml methyl-t-butyl ether to the methanolic mother liquor, which product was isolated and dried as above.

Yield: 3.12 g (6.2%) [α]$^{20}_D$: −0.1° (c=2, MeOH)

EXAMPLE 7

Racemization of 2-(t-butyl)-3-methyl-1,3-imidazolidine-4-one hydrochloride 50.0 g (0.26 mole) 2-(t-butyl)-3-methyl-1,3-imidazolidine-4-one hydrochloride [α]$^{20}_D$: +28.1°) were suspended in 550 ml diethylene glycol dimethyl ether ("Diglyme") and heated for 5.5 hours to 130° C. After the mixture had cooled down to 20° C., the solid was filtered off, washed colorless with n-hexane and dried at 50° C. in a vacuum drying oven.

Yield: 45.5 g (91.0%) [α]$^{20}_D$: +0.5° (c=2, MeOH)

The 2-(t-butyl)-3-methyl-1,3-imidazolidine-4-one hydrochloride was recrystallized out of 160 ml ethanol and isolated and dried as above.

Yield: 36.2 g (72.4%) [α]$^{20}_D$: +0 (c=2, MeOH) Analytical data: See Example 1.

EXAMPLE 8

Enantiomeric separation of (R,S)-2-(t-butyl)-3-methyl1,3-imidazolidine-4-one after cyclization with (R)-mandelic acid The Schiff's base was produced from 38.1 g (1.25 moles) monomethylamine, 310 ml methanol, 62.8 g (0.50 mole) glycine methylester hydrochloride, 125 and 150 ml cyclohexane as entraining agent, 83.5 ml (0.75 mole) pivalaldehyde and 50.7 g (0.5 mole) triethylamine, as described in Example 1. This base was taken up in 50 ml ethanol and added drop-by-drop within 15 min. at room temperature under agitation to a solution of 91.3 g (0.6 mole) (R)-mandelic acid in 200 ml ethanol while the temperature was maintained at approximately 20° C. by water cooling. The clear yellow solution was subsequently agitated 2 hours longer and the solvent was then distilled off. The oily residue was dissolved in 200 ml acetone and cooled to 5° C. After seeding, slightly yellowish (R)-2-(t-butyl)-3-methyl-1,3-imidazolidine-4-one-(R)-mandelate crystallized out which was filtered off, washed with cool acetone and dried in a vacuum drying oven at approximately 50° C.

Yield: 36.5 g (47.4%) [α]$^{20}_D$: 87.85° (c=2, EtOH)

EXAMPLE 9

Enantiomeric separation of (R,S)-2-(t-butyl)-3-methyl-1,3-imidazolidine-4-one after liberation with sodium (R)-mandelate A solution of 87.1 g (0.5 mole) sodium-(R)-mandelate in 87 ml water was added drop-by-drop to an agitated suspension of 96.4 g (0.5 mole) (R,S)-2-(t-butyl)-3-methyl-1,3-imidazolidine-4-one hydrochloride in 500 ml acetone within 15 min. After 1 hour of agitation at room temperature, the mixture was heated to 40° C., the precipitated sodium chloride filtered off, the filtrate evaporated to a low bulk of 400 g and cooled to 5° C. Then the (R)-2-(t-butyl)-3-methyl-1,3-imidazolidine-4-one-(R)-mandelate which crystallized out was filtered off, washed with 30 ml acetone and dried in a vacuum drying oven at approximately 50° C.

Yield: 38.8 g (50.3%) $[\alpha]^{20}_D$: $-88.0°$ (c—2, EtOH)

EXAMPLE 10

Preparation of (S)-1-benzoyl-2-(t-butyl)-3-methyl-1,3-imidazolidine-4-one 24.0 g (0.3 mole) 50% sodium hydroxide solution was added drop-by-drop to a suspension of 93.5 g (0.3 mole) (R)-2-(t-butyl)-3-methyl-1,3-imidazolidine-4-one-(R)-mandel ate in 360 ml acetone under agitation. After 2 hours of agitation at room temperature, the insoluble sodium-(R)-mandelate was filtered off, washed with 150 ml acetone and dried in a vacuum drying oven at 50° C.

Yield: 47.32 g (90.6%) $[\alpha]^{20}_D$: $-142.1°$ (c=2 N HCl)

The filtrate was combined at 0° C. with a further 24.0 g (0.3 mole) 50% of sodium hydroxide solution and then drop-by-drop with 46.4 g (0.33 mole) benzoyl chloride. After 1 hour of agitation at room temperature, the precipitated common salt was filtered off and washed with 100 ml acetone. The filtrate was rotated in, the residue was dissolved in 300 ml of hot toluene, washed while hot with 100 ml water, 100 ml saturated sodium hydrogen carbonate solution and again 100 ml water and evaporated to a low bulk of approximately 150 g. Colorless crystals were produced during cooling to $-40°$ C. which were removed by suction, washed with 2×10 ml toluene, dried in a vacuum drying oven at 50 and 75° C. and recrystallized again from 120 ml ethanol. Colorless needles were obtained after filtration and drying.

Yield: 57,47 g (73.6%) melting point: 143°–146° C.

EXAMPLE 11

Preparation of (S)-1-(t-butoxycarbonyl)-2-(t-butyl)-3-methyl-1,3-imidazolidine 4-one in a two-phase system 30.8 g (0.10 mole) (R)-2-(t-butyl)-3-methyl-1,3-imidazolidine-4-one-(R)-mandelate were suspended in 300 ml n-hexane and combined with 33.3 ml (0.10 mole) 3N sodium hydroxide solution, during which two clear phases formed. Then 24.0 g (0.11 mole) di-(t-butyl)-pyrocarbonate dissolved in 50 ml n-hexane were added drop-by-drop with agitation and ice cooling within 30 min. The mixture was then agitated 1 hour more without cooling, the aqueous phase was then separated and combined with 8.3 ml concentrated hydrochloric acid. Colorless crystals of (R)-mandelic acid were obtained in a refrigerator which were removed by suction and dried in a vacuum drying oven at 50° C.

Yield: 13.0 g (85.5%) $[\alpha]^{20}_D$: $-147.3°$ (c=2, H₂O)

The organic phase was extracted three times more with 50 ml water, evaporated to a low bulk of 45 g and brought to crystallization overnight in a refrigerator. The precipitated crystals were removed by suction, washed with a little n-hexane and dried in a vacuum drying oven at room temperature. Evaporation to low bulk of the mother liquor yielded a further charge of crystals which was isolated and dried as above.

Yield: 19.8 g (77.2%) $[\alpha]^{20}_D$: $-14.6°$ (c=1, methylene chloride)

What is claimed is:

1. In a method of producing enantiomerically pure 1,3-imidazolidine-4-ones having the formula:

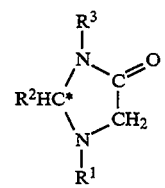

in which * is a center of asymmetry to which the enantiomeric purity refers, $R_1$ is H, $R_2$ is a sterically hindering group containing at least 3 carbon atoms and $R_3$ is an alkyl or aralkyl group containing 1–10 carbon atoms by racemic resolution of a racemic 1,3-imidazolidine-4-one having the formula:

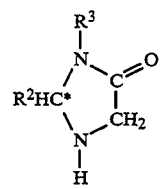

in which $R_2$ and $R_3$ have the meaning already indicated; the improvement which comprises contacting a salt of the 1,3-imidazolidine-4-one of Formula II with a base and a solvent in which the 1,3-imidazolidine-4-one of Formula II is soluble, thereby precipitating a salt of the cation of said base and the anion of said salt of said 1,3-imidazolidine-4-one, and separating the precipitated salt.

2. A method according to claim 1 in which the desired enantiomer is isolated by crystallization with 0.5–0.8 equivalent of an optically active acid relative to the 1,3-imidazolidine-4-one of Formula II.

3. A method of producing enantiomerically pure 1,3-imidazolidine-4-ones having the Formula:

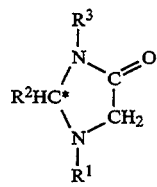

in which * is a center of asymmetry to which the enantiomeric purity refers, $R_3$ is hydrogen, $R_2$ is a sterically hindering group containing at least 3 carbon atoms and $R_3$ is an alkyl or aralkyl group containing 1–10 carbon atoms by racemic resolution of a racemic 1,3-imidazolidine-4-one having the formula:

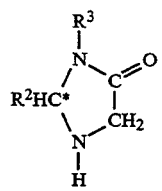  II in which $R_2$ and $R_3$ have the meaning already indicated, the desired enantiomer being obtained by crystallization with an optically active acid;

the improvement which comprises combining the crystallized, enantiomerically pure salt of the 1,3-imidazolidine-4-one of Formula II and of the optically active acid with a base and a solvent in which the 1,3-imidazolidine-4-one of Formula II is soluble thereby precipitating a salt of the cation of said base and the anion of said optically active acid, and separating the precipitated salt.

4. A method as set forth in claim 3 in which the enantiomerically pure product is substituted in the solvent.

5. A method according to claim 3 in which the dissolved product is substituted, with a group which can be spit off under acid conditions, in a solvent which is not freely miscible with water and from which the final product can be crystallized and is subsequently crystallized after it has been washed with water.

6. A method according to claim 3 in which the dissolved product is substituted with a group which can spit off under acidic conditions, in a solvent which is not freely miscible with water and from which the final product can be crystallized, and is subsequently crystallized after a part of the solvent has been removed.

7. A method as set forth in claim 1 or claim 2 in which the undesired enantiomer remaining during the crystallization is isolated as a free base or a salt, combined with an inert high boiling solvent and racemized at a temperature between 50° C. and 5° K. below the decomposition point of the free base or the salt.

8. A method of producing enantiomerically pure 1,3-imidazoldine-4-ones having the Formula:

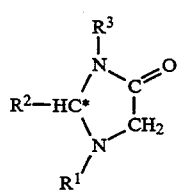  I in which * is a center of asymmetry to which the enantiomeric purity refers, $R_1$ is a group which can split off under acid conditions, $R_2$ is a sterically hindering group which contains at least 3 carbon atoms and $R_3$ is an alkyl or aralkyl group which contains 1-10 carbons atoms by means of the racemic resolution of a racemic 1,3-imidazolidine4-one having the Formula:

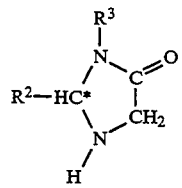  II in which $R_2$ and $R_3$ have the meaning already indicated and subsequent substitution of the hydrogen on the nitrogen of the enantiomer obtained to introduce the group which can split off under acidic conditions;

the improvement in which the crystallized enatiomerically pure salt of the 1,3-imidazolidine-4-one of Formula II and of the optically active acid is dissolved in an aqueous-organic 2-phase system containing a stoichiometric amount of a base and is subsequently substituted with the group which can be spit off under acidic conditions without separating the aqueous phase before the substitution.

9. The method according to claim 8, characterized in that the imidazolidinone of formula II in the aqueous-organic 2-phase system exhibits a distribution coefficient >1 (water/solvent).

10. The method according to claim 8 or 9, characterized in that the imidazolidinone of formula I is crystallized out of the organic solvent of the 2-phase system, optionally after evaporation to low bulk.

11. A method of producing enantiomerically pure 1,3-imidazolidine-4-ones having the General Formula:

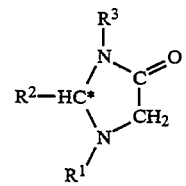  I in which * is a center of asymmetry to which the enantiomeric purity refers, $R_1$ is H, $R_2$ is a sterically hindering group which contains at least 3 carbon atoms and $R_3$ is an alkyl or aralkyl group which contains 1-10 carbon atoms which comprises cyclizing a compound having the Formula:

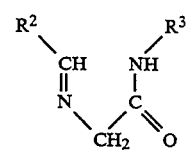  IV in the presence of an acid to form a 1,3-imidazolidine-4-one having the Formula:

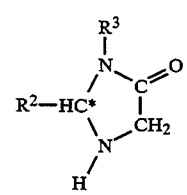  II in which the groups $R_1$ and $R_2$ have the significance indicated above, separating an enantiomer by means of crystallization with an optically active acid; the improvement in which the optically active acid is used for the cyclization and a salt of the 1,3-imidazolidine-4-one of Formula II and of the optically active acid is formed, which is subsequently isolated in enantiomerically pure form by crystallization.

* * * * *